US007514213B2

(12) United States Patent
Qu et al.

(10) Patent No.: US 7,514,213 B2
(45) Date of Patent: Apr. 7, 2009

(54) COMPOSITIONS AND METHODS FOR DETERMINING GENOTYPES

(75) Inventors: Kevin Z. Qu, Irvine, CA (US); Anthony Sferruzza, San Clemente, CA (US)

(73) Assignee: Quest Diagnostics Investments Incorporated, Wilmington, DE (US)

(*) Notice: Subject to any disclaimer, the term of this patent is extended or adjusted under 35 U.S.C. 154(b) by 938 days.

(21) Appl. No.: 10/714,508

(22) Filed: Nov. 14, 2003

(65) Prior Publication Data

US 2004/0142360 A1 Jul. 22, 2004

Related U.S. Application Data

(60) Provisional application No. 60/426,639, filed on Nov. 15, 2002.

(51) Int. Cl.
*C12Q 1/68* (2006.01)

(52) U.S. Cl. .......................... 435/6; 435/91.2

(58) Field of Classification Search ....................... None
See application file for complete search history.

(56) References Cited

U.S. PATENT DOCUMENTS

| 5,359,045 A | 10/1994 | Soubrier et al. | |
| 5,736,323 A * | 4/1998 | Soubrier et al. | ................ 435/6 |
| 6,008,373 A | 12/1999 | Waggoner et al. | |

| 2003/0158090 A1* | 8/2003 | Pedersen-Bjergaard et al. 514/3 |

OTHER PUBLICATIONS

Lindpainter et al., NEJM, 1995, vol. 332, No. 11, p. 706-711).*
Teranishi et al. Journal of Hypertension, 1999, vol. 17, p. 351-356.*
Lin et al. Clinical Biochemistry, 2001, vol. 34, p. 661-666.*
van Bockxmeer et al. Circulation, 1995, vol. 92, p. 2066-71.*
Shanmugam et al. PCR Methods and Applications, 1993, vol. 3, p. 120-121.*
Odawara et al. Human Genetics, 1997, vol. 100, p. 163-166.*
Frishberg et al. Kidney International, 1998, vol. 54, p. 1843-2849.*
Osterop et al. Hypertension, 1998, vol. 32, p. 825-830.*
Buck et al. Biotechniques (1999) 27(3):528-536.*
Montgomery et al. Circulation, 1997, vol. 96, p. 741-747.*

(Continued)

*Primary Examiner*—Gary Benzion
*Assistant Examiner*—Stephanie K Mummert
(74) *Attorney, Agent, or Firm*—Foley & Lardner LLP (57) ABSTRACT

The present invention provides methods for determining the genotype of a selected gene present in at least two alleles in a sample. The methods involve amplifying DNA from the sample with a first pair of flanking primers that hybridize to nucleic acid sequences flanking a variant-specific gene sequence, the presence of which indicates the presence of a first gene variant, and the absence of which indicates the presence of a second gene variant. The DNA is also amplified with a third primer that specifically binds to the variant-specific sequence and together with one of the flanking primers forms a second pair of primers. Detection of one or more nucleic acid products of the amplification reaction is indicative of the genotype present in the sample.

34 Claims, 1 Drawing Sheet

"I" variant:

presence of variant region

"D" variant absence of variant region

Relative size and identity of amplification products:

I/I genotype

D/D genotype

I/D genotype

OTHER PUBLICATIONS

Sequence alignment, Seq Id No. 1.*

Amant et al., "D allele of the angiotensin I-converting enzyme is a major risk factor for restenosis after coronary stenting." Circulation, 96:56-60 (1997).

Beohar et al., "Angiotensin-I converting enzyme genotype DD is a risk factor for coronary artery disease." J Investing Med 43:275-280 (1995).

Cambien et al., "Delection polymorphism in the gene for angiotensin-converting enzyme is a potent risk factor for myocardial infarction." Nature 359: 641-44 (1992).

Canbien, "The antiotensin-converting enzyme (ACE) genetic polymorphism: Its relationship with plasma ACE level and myocardial infarction." Clin Genetic; 46:94-101 (1992).

Dakik et al. "Association of angiotensin I-converting enzyme gene polymorphism with myocardial ischemia and patency on infarct-related artery in patients with acute myocardial infarction." J Am Coll Cardiol, 29:1468-73 (1997).

de Azevedo et al., "ACE and PC-1 gene polymorphisms in normoalbuminuric Type 1 diabetic patients: A 10-year prospective study." J Diabetes and Its Compl;16:255-262 ,(2002).

Dolnik, "DNA sequencing by capillary electrophoresis (review)." J Biochem. Biophys. Meth. 41:103-19, (1999).

Dovichi and Zhang, DNA Sequencing by capillary array electrophoresis. Meth. Mol. Biol. 167:225-39, (2001).

Gardemann et al., "ACE I/D gene polymorphism: presence of the ACE A allele increases the risk of coronary artery disease in younger individuals." Atherosclerosis, 139:153-159 (1998).

Grifa et al., Screening of neurofibromatosis type 1 gene : identification of a large deletion and of an intronic variant. Clin. Genet. 47: 281-84 (1995).

Hafner et al., Isothermal amplification and multimerization of DNA by Bst DNA polymerase. Biotechniques Apr. 30(4):852-6, 858, 860 passim (2001).

Heller, Principles of DNA separation with capillary electrophoresis Electrophoresis 22:629-43, (2001).

Higaki et al., "Deletion allele of antiotensin-converting enzyme gene increases risk of essential hypertension in Japanese men: The Suita Study." Circulation 101: 2060-65 (2000).

Kampke et al., Efficient primer design algorithms, Bioinformatics 17: 214-225 (2001).

Kennon et al., Angiotensin-converting enzyme gene and diabetes mellitus. Diabet. Med. 16: 448-58 (1999).

Kurland et al., Angiotensin converting enzyme gene polymorphism predicts blood pressure response to angiotensin II receptor type 1 antagonist treatment in hypertensive patients. J. Hypertens. 19: 1783-87 (2001).

Marian et al., "Interactions between angiotensin-I converting enzyme insertion/deletion polymorphism and response of plasma lipids and coronary atherosclerosis to treatment with fluvastatin." J Am Coll Cardiol 35:89-95 (2000).

McNamara et al., "Pharmacogenetic interactions between B-blocker therapy and the angiotensin-converting enzyme deletion polymorphism in patients with congestive heart disease." Circulation 103:1644 1648 (2001).

Mitchelson, The application of capillary electrophoresis for DNA polymorphism analysis Methods Mol. Biol, 162:3-26, (2001).

Morris and Zee, Similarity of blood pressure for each genotype of the insertion/deletion polymorphism of the dipeptidyl carboxypeptidase-1 gene in different age groups of patients with severe, familial essential hypertension. Clin. Exp. Pharmacol., Physiol. 21:919-24 (1994).

O'Malley et al., "Angiotensin-converting enzyme DD genotype and cardiovascular disease in heterozygous familial hypercholesterolemia." Circulation 97:1780-1783 (1998).

Odawara et al., Mistyping frequency of the angiotensin-converting enzyme gene polymorphism and an improved method for its avoidance. Hum. Genet. 100: 163-66 (1997).

Okamura et al., "Pharmacogenetic analysis of the effect of angiotensin-converting enzyme inhibitor on restenosis after percutaneous transluminal coronary angioplasty." Angiology, 50:811-822 (1999).

Okumura et al., Quinapril prevents restenosis after coronary stenting in patients with angiotensin-converting enzyme D allele. Circ. J. 66: 311-316 (2002).

Pfohl et al., "Insertion/deletion polymorphism of the antiotensin I-converting enzyme gene is associated with coronary artery plaque calcification as assessed by intravascular ultrasound." JACC 1998; 31:987-991.

Protonotarios et al., Genotype-phenotype assessment in autosomal recessive arrhythmogenic right ventricular cardiomyopathy (Naxos Disease) caused by a deletion in plakoglobin J. Am. Coll. Cardiol. 38: 1477-84 (2001).

Ribichini et al., Plasma activity and insertion/Deletion polymorphism of angiotensin I-converting enzyme. Circulation 97: 147-54 (1998).

Rigat et al., PCR detection of the insertion/deletion polymorphism of the human angiotensin converting enzyme gene (DCP1) (dipeptidyl carboxypeptidase 1) Nucl. Acid Res. 20: 1433 (1992).

Ruiz et al., "Insertion/deletion polymorphism of the angiotensin-converting enzyme gene is strongly associated with coronary heart disease in non-insulin-dependent diabetes mellitus." Proc Natl Acad Sci USA 3662-3665 (1994).

Saiki, "Amplification of Genomic DNA" in PCR Protocols, Innis et al., Eds., Academic Press, San Diego, CA 1990, pp. 13-20.

Shanmugan et al., Mistyping ACE heterozygotes. PCR Methods Applications 3: 120-21 (1993).

van der Weide and Steijns, Cytochrome P450 enzyme system: genetic polymorphisms and impact on clinical pharmacology. Ann. Clin. Biochem. 36: 722-29 (1999).

Wharam et al., Specific detection of DNA and RNA targets using a novel isothermal nucleic acid amplification assay based on the formation of a three-way junction structure. Nucleic Acids Res. Jun. 1; 29(11):E54-E54 (2001).

Winkelmann et al., "Pharmacogenomics and Complex Cardiovascular Diseases—Clinical Studies in Candidate Genes," in Pharmacogenomics, Licinio and Wong, eds., pp. 251-261, Wiley-VCH, (2002).

Zee et al., Insertion variant in intron 9, but not microsatellite in intron 2, of the insulin receptor gene is associated with essential hypertension. J. Hypertens. Suppl. 12: S13-S22 (1994).

* cited by examiner

*Fig. 1*

"I" variant:

presence of
variant region

"D" variant absence of
variant region

Relative size and identity of
amplification products:

I/I genotype

D/D genotype

I/D genotype

COMPOSITIONS AND METHODS FOR DETERMINING GENOTYPES

This application claims the benefit of U.S. Provisional Application No. 60/426,639, filed Nov. 15, 2002.

FIELD OF THE INVENTION

The present invention relates to the identification of the genotype of a subject, and the use of such identification for diagnostic, prognostic, and therapeutic purposes.

BACKGROUND OF THE INVENTION

The following description of the background of the invention is provided simply as an aid in understanding the invention and is not admitted to describe or constitute prior art to the invention.

Angiotensin converting enzyme (ACE) is a zinc metalloproteinase involved in the renin-angiotensin and in the kallikrein-kinin systems, in which it is responsible for the proteolytic activation of angiotensin I and bradykinin. Because of the central role played by the renin-angiotensin and kallikrein-kinin systems in regulating blood pressure and electrolyte balance, ACE has been identified as an important therapeutic target for diseases such as essential hypertension, diabetic neuropathy, renal disease, congestive cardiomyopathies including congestive heart failure, and myocardial infarction. See, e.g., Cambien et al., *Nature* 359: 641-44 (1992); U.S. Pat. No. 5,359,045; Higaki et al., *Circulation* 101: 2060-65 (2000); Kennon et al., *Diabet. Med.* 16: 448-58 (1999). ACE has also been identified as a risk factor for stent restenosis following treatment for coronary artery disease. See, e.g., Ribichini et al., *Circulation* 97: 147-54 (1998).

ACE is mainly located on the endothelium of blood vessels, especially in the pulmonary circulation, but it is also found in epithelial cells, in blood mononuclear cells, in macrophages, in male germinal cells and in a circulating form in several biological fluids. Circulating ACE probably originates from the vascular endothelial cells. In plasma and on the surface of endothelial cells, ACE converts the inactive decapeptide angiotensin I into the highly vasoactive and aldosterone-stimulating octapeptide angiotensin II. Angiotensin II is a powerful vasoconstrictor which may modulate or induce the growth of vascular smooth muscle cells and cardiomyocytes. ACE can affect the oxidation of low density lipoproteins (LDLs), endothelial cell function, and smooth muscle cell migration and proliferation, which are all important components of atherosclerosis.

The human ACE gene is located on chromosome 17q23 and includes 26 exons. Its coding sequence is 4.3 kb in length and codes for a protein of 1,306 amino acids. The ACE gene is present in the population as different allelic variants. A variant of particular interest clinically is the presence or absence of a 287 base pair ("bp") non-coding fragment within Intron 16. When this 287 bp sequence is present in an ACE gene, the genotype is designated "I" for "insertion"; conversely, when this 287 bp sequence is absent in an ACE gene, the genotype is designated "D" for "deletion." Because the genome contains two copies of each gene, referred to as "alleles," possible ACE genotypes with regard to this variant are D/D, I/D, and I/I.

Increased ACE activity correlates strongly with the deletion/deletion (D/D) and insertion/deletion (I/D) genotypes. The D/D genotype has also been associated with myocardial infarction, ischemic and idiopathic dilated cardiomyopathy, sudden death in hypertrophic cardiomyopathy, and restenosis after percutaneous transluminal coronary angioplasty. In addition, an increased risk of coronary artery disease is attributed to the ACE D/D genotype. The ACE genotype of an individual has also been related to response to ACE inhibitors (such as benazepril, captopril, cilazapril, enalapril, enalaprilat, fosinopril, lisinopril, moexipril, perindopril, quinapril, ramipril, and trandolapril) and to angiotensin II type 1 receptor antagonists (such as irbesartan, losartan, valsartan, telmisartan, camdesartam, and eprosartan). See, e.g., Kurland et al., *J. Hypertens.* 19: 1783-87 (2001); Okumura et al., *Circ. J.* 66: 311-16 (2002).

Polymerase chain reaction ("PCR") amplification, followed by agarose gel electrophoresis, is commonly used to identify the ACE genotype present in a sample. It has been reported, however, that such PCR methods result in significant mistyping. See, e.g., Odawara et al., Hum. Genet. 100: 163-66 (1997); Shanmugan et al., PCR Methods Applications 3: 120-21 (1993); Rigat et al., Nucl. Acid Res. 20: 1433 (1992). To eliminate the mistyping, a second PCR reaction that detects only the I/I and I/D genotypes is typically performed to confirm the D/D genotype. Since only the I/I and I/D genotypes can be detected in the second reaction, the absence of a PCR fragment is taken as indicating a true D/D genotype. Such methods, however, cannot distinguish an unsuccessful PCR reaction from a true D/D genotype.

Each publication and patent in the foregoing section is hereby incorporated by reference in its entirety, including all tables, figures, and claims.

SUMMARY OF THE INVENTION

The present invention provides methods and compositions for determining the genotype of a selected gene present in a sample. While described hereinafter in reference to the angiotensin converting enzyme (ACE) genotype present in a sample, the skilled artisan will readily understand that the methods described herein are generally applicable to the analysis of genes that are present in one or more allelic variants.

The methods described herein comprise amplifying DNA from the sample with a first pair of primers that hybridize to nucleic acid sequences flanking a variant-specific gene sequence; that is, a sequence, the presence of which indicates the presence of a first gene variant, and the absence of which indicates the presence of a second gene variant. A third primer is also provided that specifically binds to the variant-specific sequence and together with one of the flanking primers forms a second pair of primers. One or more nucleic acid products of the amplification are detected, and the nucleic acid products indicate the genotype present in the sample. In one embodiment, three nucleic acid products of the amplification are detected.

In preferred embodiments, the methods described herein comprise amplifying DNA from the sample with a first pair of primers that hybridize to nucleic acid sequences flanking a variant-specific ACE sequence, the presence of which indicates the presence of a first ACE gene variant, and the absence of which indicates the presence of a second ACE gene variant. A third primer is also provided that specifically binds to the variant-specific ACE sequence and together with one of the flanking primers forms a second pair of primers. One or more nucleic acid products of the amplification are detected, and the nucleic acid products indicate the ACE genotype present in the sample. In one embodiment three nucleic acid products of the amplification are detected.

In addition to the ACE gene, the present invention may be adapted to determine the gene variants present in any gene of interest. Preferably, the gene variants comprise the presence or absence of a particular sequence. For example, insertion/deletion variants are known to those of skill in the art in genes encoding cytochrome P450 enzymes (e.g., van der Weide and Steijns, Ann. Clin. Biochem. 36: 722-29 (1999)); insulin receptors (e.g., Zee et al., J. Hypertens. Suppl. 12: S13-22 (1994)); neurofibromatosis type 1 (e.g., Grifa et al., Clin. Genet. 47: 281-84 (1995)); plaktoglobin (e.g., Protonotarios et al., J. Am. Coll. Cardiol. 38: 1477-84 (2001)); dipeptidyl carboxypeptidase-1 (e.g., Morris and Zee, Clin. Exp. Pharmacol., Physiol. 21: 919-24 (1994)); etc.

In various preferred embodiments, the methods involve contacting a sample of DNA from a subject, most preferably a human, with primers selected to amplify a region of the ACE gene containing a sequence that is indicative of the ACE variant present. The primers consist of two forward primers and one reverse primer (or, alternatively, two reverse primers and one forward primer). Each of the forward (reverse) primers form a primer pair with the reverse (forward) primer. The first primer pair flanks the sequence that is indicative of the ACE variant (e.g., a sequence that may be inserted in the ACE gene in certain genotypes); thus, amplification by this primer pair provides an amplicon, regardless of the presence or absence of the variant sequence (e.g., the potential insertion). The second primer pair contains one primer within the sequence that is indicative of the ACE variant (e.g., the potential inserted sequence); thus, amplification by this primer pair will only occur if the ACE variant is present. In one embodiment the sample is un-degraded DNA. By "un-degraded DNA" is meant a sample of DNA having a population of DNA similar to that derived from live tissue. Live tissue contains un-degraded DNA, as do samples of DNA derived from live tissue or tissue that has died very recently. Persons of ordinary skill know that when cells die the DNA begins to degrade and forms different gel patterns (e.g., in a polyacrylamide or other size-differentiating gel) than samples of DNA derived from live tissue, due to the fragmentation of DNA strands in the sample that form as DNA begins to degrade. Thus, in various embodiments un-degraded DNA will contain at least 70% or at least 80% or at least 90% of the DNA strands found in a corresponding sample from live tissue, which contains un-degraded DNA. In various embodiments the live tissue can be, for example, blood, cultured cells, cells derived from amniotic fluid, or cells derived from chorionic villi.

Figure 1:
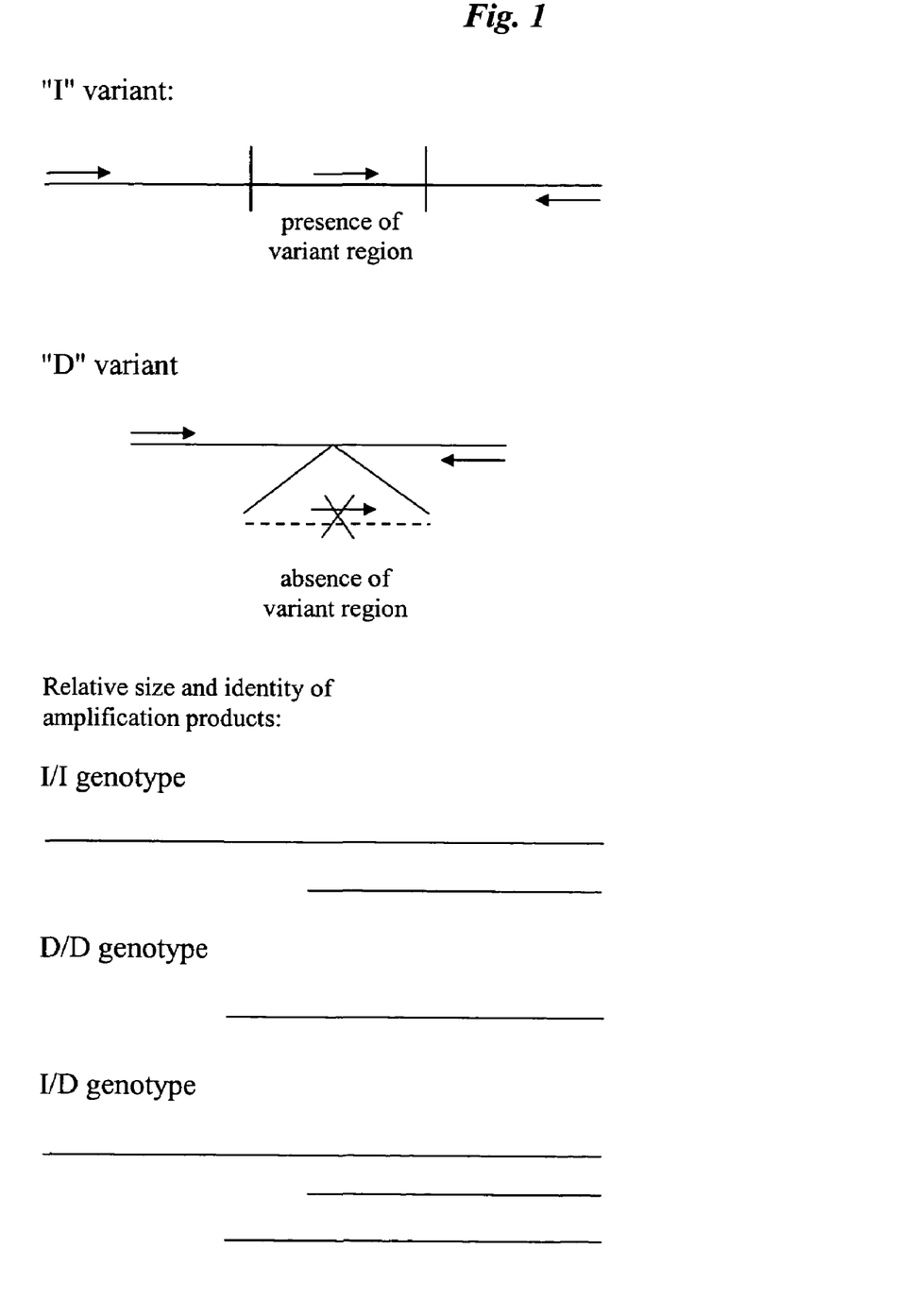
FIG. 1 provides a schematic representation of the genotyping assays described herein, with reference to identification of a genotype related to a deletion/insertion variant. The amplification primers are shown as arrows, with the direction of the arrow indicating the direction of primer extension.

The present invention is described below in terms of the 287 base pair ("bp") non-coding fragment within Intron 16 that is referred to by the artisan as the I/D polymorphism. A polymerase chain reaction amplification of the sample of DNA is performed with replication of the DNA being initiated by the three primers described above. In this preferred embodiment, the size of the first amplicon is indicative of the presence or absence of the inserted sequence, and hence whether the D or I variant is present. The presence of the second amplicon verifies the presence of the I variant, while the absence of the second amplicon verifies the presence of the D variant. Thus, the nucleic acid products of the PCR amplification are detected, and the genotype is determined based on the nucleic acid products of the PCR amplification:

"I" variant:

The arrows represent the amplification primers and indicate the direction of primer extension "D" variant deleted 287 bp I/D region By "variant-specific ACE sequence" is meant a nucleic acid sequence that, when present or absent, correlates to a particular ACE variant present in a particular genotype. For example, in the most preferred embodiment the variant-specific ACE sequence is a 287 base pair insertion/deletion polymorphism referred to as "ACE I/D." In a normal diploid eukaryote, each gene has two loci, i.e., one gene copy at the same locus (position) on each of two matched chromosomes. Different versions of a gene can occur at any locus, and these versions are called alleles. Each allele may be the wild-type (normal) allele or an allelic variant. Thus, two different versions of a ACE gene will be present in any particular subject's genome.

By "allelic variant" is meant a variation in a nucleotide sequence, such as a single nucleotide polymorphism (SNP), a multiple nucleotide polymorphism, or any other variant nucleic acid sequence or structure (e.g., duplications, deletions, inversions, insertions, translocations, etc.) in a gene that alters the activity and/or expression of the gene, or correlates with the occurrence of a disease or unhealthy state. Allelic variants can over- or under-express the polypeptide encoded by the gene, and/or express proteins with altered activities by virtue of having amino acid sequences that vary from wild-type sequences. Allelic variants need not occur in a coding sequence since variants at non-coding or nonsense sequences also can correlate with the occurrence of a disease or unhealthy state.

By "flanking primers" is meant one or more primers that hybridize at either side of a nucleic acid sequence of interest, but not within the sequence of interest itself. Such primers serve as the starting points of nucleic acid replication by a DNA polymerase, e.g., in an amplification reaction such as PCR.

In the present invention, a preferred allelic variant is a polymorphism of the ACE gene, which is the presence or absence of the 287 base pair nonsense DNA domain within Intron 16. Thus, a "first ACE gene variant" may represent, e.g., the "I" variant containing the 287 base pair nonsense DNA domain. Similarly, a "second ACE gene variant" may represent the "D" variant that does not contain the 287 base pair nonsense DNA domain. As discussed above, the three potential ACE genotypes associated with this 287 base pair sequence are known to those of skill in the art as I/I (for insertion/insertion; that is, each allele contains the sequence); I/D (for insertion/deletion; that is, one allele contains the insertion and one does not); and D/D (for deletion/deletion; that is neither allele contains the insertion). See, e.g., Winkelmann et al., "Pharmacogenomics and Complex Cardiovascular Diseases—Clinical Studies in Candidate Genes," in *Pharmacogenomics*, Licinio and Wong, eds., pp. 254-61, Wiley-VCH, 2002.

The definitions above are not meant to exclude allelic variants that have yet to be discovered and which correlate with a disease or unhealthy state. The person of ordinary skill will realize that other allelic variants are possible and may be used in a similar manner.

Often, more than one allelic variant exists and persists in a population of individuals. By "exist and persist" it is meant that the frequency of incidence of a rare allele(s) is greater than can be explained by recurrent mutation alone (i.e., typically greater than 1%). However, the frequency of any variant allele may vary over time due to such factors as genetic drift and the like. When two or more different alleles of a gene are present in a population, the gene or the protein it encodes is said to be polymorphic. As used herein, a "polymorphism" refers to a specific form of a gene or protein.

As used herein, the numeric order of a sequence is assigned to the antisense strand of the sequence from 5' to 3' in increasing number. A "forward primer" as used herein is a primer whose sequence of nucleotides corresponds to a sequence this antisense strand; a "reverse primer" is a primer whose sequence corresponds to the complement of this strand (i.e., is of the same sense as the sense strand of the gene). The skilled artisan will understand that the designation of a primer as being "forward" or "reverse" is arbitrary, but that a "forward" primer in a primer pair will initiate DNA synthesis on one strand of the target DNA towards the "reverse" primer, while a "reverse" primer will initiate DNA synthesis on the complementary strand of the target DNA towards the "forward" primer.

The "target sequence" is a site where the primer hybridizes to the DNA and provides a site for DNA synthesis to begin by one or more DNA polymerases.

By "DNA synthesis being initiated by the primers" is meant that DNA synthesis begins at the site where a primer hybridizes with a strand of DNA and provides a start point for a DNA polymerase to begin DNA synthesis in an amplification reaction.

By "amplicon" is meant one or more copies of a nucleic acid sequence that has been amplified by an amplification method such as PCR.

The methods described herein are discussed in reference to polymerase chain reaction ("PCR") amplification of genomic sequences. The skilled artisan will understand, however, that numerous methods are known in the art for amplification of nucleic acids, and that these methods may be used either in place of, or together with, the disclosed PCR steps. Nucleic acid amplification methods, such as PCR, isothermal methods, rolling circle methods, etc., are well known to the skilled artisan. See, e.g., Saiki, "Amplification of Genomic DNA" in *PCR Protocols*, Innis et al., Eds., Academic Press, San Diego, Calif. 1990, pp 13-20; Wharam et al., *Nucleic Acids Res.* 2001 June 1;29(11):E54-E54; Hafner et al., *Biotechniques* 2001 April;30(4):852-6, 858, 860 passim; Zhong et al., *Biotechniques* 2001 April;30(4):852-6, 858, 860 passim.

The term "biological sample" as used herein refers to a sample obtained from a biological source, e.g., an organism, cell culture, tissue sample, etc. A biological sample can, by way of non-limiting example, consist of or comprise blood, sera, urine, feces, epidermal sample, skin sample, cheek swab, sperm, amniotic fluid, cultured cells, bone marrow sample and/or chorionic villi. The DNA samples used in the methods described herein can be taken from any source, but in preferred embodiments is from one of the following sources: the endothelium of blood vessels, epithelial cells, blood mononuclear cells, macrophages, and a biological fluid.

The term "subject" as used herein refers to any eukaryotic organism. Preferred subjects are fungi, plants, invertebrates, insects, arachnids, fish, amphibians, reptiles, birds, marsupials and mammals. A mammal can be a cat, dog, cow, pig, horse, ox, elephant, or simian. Most preferred subjects are humans. A subject can be a patient, which refers to a human presenting to a medical provider for diagnosis or treatment of a disease. The term "animals" includes prenatal forms of animals, such as fetuses.

As used herein, a "plurality of samples" refers to at least two. Preferably, a plurality refers to a relatively large number of samples. A plurality of samples is from about 5 to about 500 samples, preferably about 25 to about 200 samples, even more preferably from about 50 to about 200 samples, and most preferably from about 50 to about 100 samples. The term "about" in this context refers to +/−10% of a given number. Samples that are processed in a single batch run of the method of the invention are usually prepared in plates having 24, 48, 96, 144, or 192 wells. The term "samples" includes samples per se as well as controls, standards, etc. that are included in a batch run.

Many embodiments of the methods are possible. In preferred embodiments, the method includes the performance of a single polymerase chain reaction amplification, the subject is a human, and the sample is a human sample. In preferred embodiments, the genotype is described as one of the following: insertion/insertion, insertion/deletion, or deletion/deletion. In particularly preferred embodiments, the genotype is determined by detecting the presence of a polymorphism that resides on Intron 16 of chromosome 17q23, and the polymorphism is the presence or absence of a 287 base pair nonsense DNA domain.

In various preferred embodiments, the nucleic acid products that are detected are a 157 base pair nucleic acid fragment and a 410 base pair nucleic acid fragment, indicating that the genotype is I/I; a 123 base pair fragment, a 157 base pair nucleic acid fragment, and a 410 base pair nucleic acid fragment, indicating that the genotype is I/D; and a 123 base pair nucleic acid fragment, indicating that the genotype is D/D. Thus, in the preferred embodiments the genotype is determined by detecting the presence or absence of these nucleic acid products. In other embodiments where different primers are used, the nucleic acid products that are detected are an approximately 157 base pair nucleic acid fragment and an approximately 410 base pair nucleic acid fragment, indicating that the genotype is I/I; an approximately 123 base pair fragment, an approximately 157 base pair nucleic acid fragment, and an approximately 410 base pair nucleic acid fragment, indicating that the genotype is I/D; and an approximately 123 base pair nucleic acid fragment, indicating that the genotype is D/D. By "approximately" is meant plus or minus 10%. In another embodiment the strands correspond to the stated lengths plus or minus 20%.

In another aspect, the invention provides substantially purified nucleic acids that may be used for amplifying DNA from the ACE region of a DNA sample. The nucleic acids include one or more of the following: a nucleic acid having the sequence 5'-CCA TCC TTT CTC CCA TTT CTC T-3' (SEQ ID NO: 1); a nucleic acid having the sequence 5'-GGA TGG TCT CGA TCT CCT GA-3' (SEQ ID NO: 2); and a nucleic acid having the sequence 5'-CCT TAG CTC ACC TCT GCT TGT AA-3' (SEQ ID NO: 3).

One or more nucleic acids of the set can be labeled with a detectable "tag" or identifying reagent. In preferred embodiments, one or more primers, most preferably the primer set forth in SEQ ID NO: 3 is labeled with a detectable label, in preferred embodiments at the 5' end with 6-FAM (fluorescein) or another fluorescent reagent. Preferably, the present invention provides two, and most preferably, each of the three nucleic acids in a single container or environment, such as an aqueous solution.

Preferably, a nucleic acid for use as a primer in the present invention binds in a complementary fashion to a portion of a nucleic acid sequence that correlates with the ACE genotype present in the sample, or that will be extended into such a sequence by primer extension. Primers must be of a length sufficient to provide specific binding to the target sequence of interest. Such primers comprise an exact complement to the sequence of interest for 15 to 75 nucleotides in length, preferably 17 to 50 nucleotides in length, and more preferably from 20 to 30 nucleotides in length.

As used herein, the term "purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "purified" oligonucleotide is preferably at least 10% pure. A "substantially purified" oligonucleotide is preferably at least 50% pure, more preferably at least 75% pure, and most preferably at least 95% pure.

In another aspect the present invention provides kits for determining the genotype for angiotensin converting enzyme (ACE) in a mammal. The kits include one or more substantially pure nucleic acids of the invention, optionally include one or more solvents and/or reagents useful in conducting assays to determine the genotype for angiotensin converting enzyme (ACE), and optionally include one or more containers for conducting assays and/or mixing the reagents. Preferably, such kits contain primers in an amount sufficient to perform an assay on at least one sample for determining the ACE genotype in the sample, and more preferably in an amount sufficient to perform an assay on a plurality of samples. In preferred embodiments, the elements of the kit are contained in an enclosure, such as a wrapping or box. In certain other embodiments, the kits may also contain an instruction manual providing instructions for use of the primers or other kit materials in conducting the assays.

In various aspects of the present invention, the genotyping methods described herein may be used to identify subjects at risk for diseases such as essential hypertension, diabetic neuropathy, renal disease, congestive cardiomyopathies including congestive heart failure, and myocardial infarction, or at risk for adverse outcomes from treatment, such as stent restenosis following treatment for coronary artery disease, or poor (or heightened) responsiveness to pharmaceutical intervention, such as treatment with ACE inhibitors (such as benazepril, captopril, cilazapril, enalapril, enalaprilat, fosinopril, lisinopril, moexipril, perindopril, quinapril, ramipril, and trandolapril) or angiotensin II type 1 receptor antagonists (such as irbesartan, losartan, valsartan, telmisartan, camdesartam, and eprosartan). In these aspects, the genotype of a subject is determined, and the predisposition to disease or the risk of an adverse outcome associated with that genotype is assigned to the subject.

In various preferred embodiments, the invention provides methods of identifying a patient with a heightened risk of suffering from a disease selected from the following: myocardial infarction, ischemic and idiopathic dilated cardiomyopathy, sudden death in hypertrophic cardiomyopathy, and restenosis after percutaneous transluminal coronary angioplasty, based upon the identified ACE genotype of the subject. By "heightened risk" is meant that the patient's medical risk of suffering from a particular disease increased relative to the general population. In preferred embodiments, the heightened risk is at least one standard deviation, more preferably two standard deviations, and most preferably three standard deviations greater than that present in the general population.

In various other preferred embodiments, the invention provides a method for selecting a treatment regimen for a particular subject, based upon the identified ACE genotype of the subject. A "treatment regimen" is a course of treatment that may include, but is not limited to, drug therapy, changes to lifestyle, changes to diet, surgical intervention, installation of shunts, β-blockers (such as betaxolol and metipranolol), prostaglandin analogs, osmotic diuretics, and combinations of these or other treatments.

In yet other preferred embodiments, the invention provides a method for selecting one or more subjects for inclusion in a clinical trial, based upon the identified ACE genotype of the subject(s). In these embodiments, subjects may be excluded or included from the trial, according to their heightened risk of suffering from a disease and/or their predicted responsiveness to a particular treatment regimen.

The summary of the invention described above is non-limiting and other features and advantages of the invention will be apparent from the following detailed description of the invention, and from the claims.

DETAILED DESCRIPTION OF THE INVENTION

The present invention provides methods and compositions for accurately determining the genotype of a gene of interest in a single amplification reaction and with a minimum of required reagents. As described in detail herein, preferably a primers pair is employed that hybridize to nucleic acid sequences that flank a variant-specific gene sequence. The variant-specific gene sequence is preferably a 287 base pair insertion/deletion polymorphism in the ACE gene that is a nonsense DNA domain within Intron 16 of the ACE gene, the presence or absence of which correlates with the ACE I/D genotype. In addition to the two flanking primers, a third primer is also used. The third primer hybridizes within the variant-specific sequence and forms a second pair of primers with one of the flanking primers. The nucleic acid products of the amplification are produced, detected, and correlated to a genotype. FIG. 1 provides a schematic depiction of the amplification scheme described above.

The human ACE intron 16 nucleic acid sequence (antisense) for the I variant is as follows (SEQ ID NO: 4). An exemplary forward primer sequence (SEQ ID NO: 1) is underlined italic, while the complement to an exemplary reverse primer (SEQ ID NO: 3) is underlined

```
  1 gtgagagctc atgtgcaggc tgagtgagag gcgagggctg ggactggcat ggggcccggg 61 ggtgctgggt gagagcacag agttgggctc ccctcgctct tggggtcagc gtgcccagga 121 aatgcccttt cttgttttcc acgaggggg cttctctgcc cactgagagc cggcacctac 181 ttcataccat gccccgatca gctgccctc cctcagaacc gccctctgct taagggtgtc 241 cactctctcc tgtcctctct gcatgccgcc cctcagagca gcgggatctc aaagttatat 301 ttcatgggct tggactccaa atgggggaa ctcggggaca ctagctcccc ccggcctcct
```

-continued

```
 361 ttcgtgaccc tgcccttgac ttcctcacct tctctgtctt tcctgagccc ctctcccagc
 421 atgtgactga taaggaaatt gagtcacaca gcccctgaaa gcgccagact agaacctgag
 481 cctctgattc ctctcacttc cctcccctac cctgccactt cctactggat agaagtagac
 541 agctcttgac tgtcctcttt tctccccact ggctggtcct tcttagcccc agcccgtttg
 601 aaagagctca cccccgacac aaggacccgc acacagatac ctcccagctc cctctcaacc
 661 cacccttttcc agggttggag aacttgaggc ataaacattc ttccatgagg aatctccacc
 721 cagaaatggg tctttctggc ccccagccca gctcccacat tagaacaatg acaaatagaa
 781 ggggaaatgg aaaataaaca ggagaaacgg ttttcccagg acagggtttg gcctacaagt
 841 tgtggatgtg ggtacccatg ccaagtgtga ggggaggctg gccgggtgtg gtggctcatg
 901 ctctaatccc agcactttgg gaggccaagg tgagtagatc acttgaggcc gggagtttga
 961 gaccagcctg gccaacatgg tgaaacccca tctgtactaa aaatacaaaa gttagctggg
1021 cgtggtggta gatgcctgta gtcccagcta cttgggaggc tgaggcatga gaatcgcttg
1081 agcccagcca gggcaataca gcaagacccc gtctctacaa ataaaataca aaaaattagt
1141 tggatgtggt ggtgcatgcc tgtagtccta gctgctaggg aggctgagat ggaaggattg
1201 cttgagcctg ggaggtcaag gctgcagtga gccgagatgg cgccactgca ctccagcctg
1261 ggcaacagag tgagaccctg tctcagaaag aaaaaaaaaa aaaaaggaga ggagagagac
1321 tcaagcacgc ccctcacagg actgctgagg ccctgcaggt gtctgcagca tgtgcccagg
1381 ccggggactc tgtaagccac tgctggagac cactcccatc ctttctccca tttctctaga
1441 cctgctgcct atacagtcac tttttttttt ttttgagac ggagtctcgc tctgtcgccc
1501 aggctggagt gcagtggcgg gatctcggct cactgcaacg tccgcctccc gggttcacgc
1561 cattctcctg cctcagcctc ccaagtagct gggaccacag cgcccgccac tacgcccggc
1621 taatttttg tatttttagt agagacgggg tttcaccgtt ttagccggga tggtctcgat
1681 ctcctgacct cgtgatccgc ccgcctcggc ctcccaaagt gctgggatta caggcgtgat
1741 acagtcactt ttatgtggtt tcgccaattt tattccagct ctgaaattct ctgagctccc
1801 cttacaagca gaggtgagct aagggctgga gctcaagcca ttcaaccccc taccag
```

The "D" variant represents the loss of an alu-type sequence from this intron in the region from nucleotide 1451 to nucleotide 1738 of the foregoing sequence. This region has the following sequence (SEQ ID NO: 5). An exemplary forward primer (SEQ ID NO: 2) for use in a primer pair with the exemplary reverse primer shown above is underlined bold:

```
  1 atacagtcac tttttttttt tttttgagac ggagtctcgc tctgtcgccc aggctggagt
 61 gcagtggcgg gatctcggct cactgcaacg tccgcctccc gggttcacgc cattctcctg
121 cctcagcctc ccaagtagct gggaccacag cgcccgccac tacgcccggc taatttttg
181 tatttttagt agagacgggg tttcaccgtt ttagccgga tggtctcgat ctcctgacct
241 cgtgatccgc ccgcctcggc ctcccaaagt gctgggatta caggcgtg
```

Amplification Reaction

The methods described herein are discussed in reference to polymerase chain reaction ("PCR") amplification of genomic sequences. As noted above, the skilled artisan will understand that numerous methods are known in the art for amplification of nucleic acids, and that these methods may be used either in place of, or together with, the disclosed PCR steps.

The objective of PCR is to amplify a specific DNA fragment, referred to as the "target sequence." Primers function in pairs, a so-called forward primer and a so-called reverse primer, with this distinction being arbitrary from the computational viewpoint. The primer pairs are chosen such that primer extension occurs towards one another to cover a given target region. PCR begins with a high temperature (95° C.) denaturation step converting the double-stranded DNA into single-stranded DNA, followed by a low temperature step (45-65° C.) during which the primers hybridize and finally an intermediate temperature step (72° C.) for the primer extension. Typically 25-45 of these cycles are performed.

Formally, primers are considered as strings over the alphabet $\Sigma=\{A, C, G, T\}$ with the set of all these strings being $\Sigma^*$. As described herein, the first position of a primer indicates the 5' end while the terminating position indicates the 3' end. Each primer is chosen within a window whose length and location is subject to the discretion of the skilled artisan.

Primer assessment extends beyond string matching and involves criteria including the proximity between primer melting temperatures, minimization of hybridization effects between forward and reverse primers, and avoidance of hybridization of primers with themselves. The latter two criteria are dealt with by annealing values. The design complexity increases in so-called multiplex PCR. This involves performing multiple PCR reactions simultaneously in a single tube. Consequently, this requires that physical parameters such as cycle number, cycle duration and annealing temperature are identical for all of the PCR reactions. Additional information regarding the design of other primers is found at "Efficient primer design algorithms," *Bioinformatics* 17: 214-225 (2001).

For each reaction mixture, the amount of the nucleic acid sufficient for primer extension can be determined by obtaining a sample comprising nucleic acid and determining the concentration of nucleic acid therein. One skilled in the art will be able to prepare such samples to a concentration and purity necessary to practice the invention, and to estimate the amount of a specific sample that should be added to a particular reaction mixture. A failure to detect a signal in the method of the invention may signify that, among other things, an inadequate amount of nucleic acid has been added to a reaction mixture. Those skilled in the art will be able to troubleshoot failed batch runs and adjust the contents of the reaction mixtures and/or conditions of the run accordingly. Control samples, both positive and negative, can be included in the batch runs to confirm that appropriate amounts of nucleic acid are present.

In the exemplary embodiments of the invention described below, three primers are used—two forward primers and one reverse primer. Forward primer 1 (SEQ ID NO: 1), which flanks the region of interest; forward primer 2 (SEQ ID NO: 2), which is specific for the insertion; and a reverse primer (SEQ ID NO: 3), which flanks the region of interest. Thus, the two forward primers share one reverse primer. In alternative embodiments, two reverse primers can be used with one forward primer without changing the principles of the invention described herein.

Applicants have determined that the "three primer, two primer pair" methods described herein can provide sensitive and specific detection of the ACE genotype present in a sample without the generation of spurious PCR products that increase the background signal obtained. It has thus been discovered unexpectedly by the inventors that utilizing a single PCR reaction with the elimination of one reverse primer results in clearer, more easily interpretable results, and the elimination of a second PCR reaction. The invention advantageously provides detection of a polymorphism in the ACE gene based on the presence or absence of a 287 base pair nonsense DNA domain within Intron 16.

The genotypes relating to the invention can be described as I/I, I/D, and D/D. The I/I (insertion/insertion) genotype indicates a subject having two alleles containing the 287 base pair insertion within Intron 16; the I/D (insertion/deletion) genotype indicates a subject having one allele containing the insertion and the other allele lacking the insertion; and the D/D genotype indicates a subject having no alleles containing the insertion.

Detection of Amplification Products

Following amplification, the resulting nucleic acid products can then be denatured (e.g., in formamide) and fractionated for detection of the products generated, e.g., by capillary electrophoresis ("CE"). In the exemplary methods described hereinafter, an ABI PRISM® 310 Genetic Analyzer (Applied Biosystems) is used with ABI PRISM® 310 Genetic Analyzer capillaries (47 cm×50 um capillaries). For reviews of the use of CE in DNA sequencing and polymorphism analysis, see Heller, *Electrophoresis* 22:629-43, 2001; Dovichi et al., *Meth. Mol. Biol.* 167:225-39, 2001; Mitchelson, *Methods Mol. Biol.* 162:3-26, 2001; and Dolnik, J *Biochem. Biophys. Meth.* 41:103-19, 1999.

Examples of other apparatuses that may be useful for electrophoresis and visualization are an agarose gel electrophoresis apparatus, such as CBS Scientific horizontal mini-gel; a power supply having a constant voltage of 100 to 200V or better variable power supply for electrophoresis, such as the BioRad Model 200; photodocumentation apparatus, such as the Alpha Innotech AlphaImager or Polaroid DS34 t; and a transilluminator, e.g., a VWR Model LM-20E or equivalent. Other methods of fractionating the amplification products can also be utilized, such as standard or HPLC chromatography methods, or nucleic acid microarray hybridization.

The different genotype alleles are then detected based on the nucleic acid fragment size. Thus, the following describes the fragment sizes obtained using the exemplary primers descried herein, and shows the corresponding genotype indicated:

| Genotype | PCR fragment (bp) |
| --- | --- |
| I/I | 157, 410 |
| I/D | 123, 157, 410 |
| D/D | 123 |

In preferred embodiments, the primer nucleic acid that is common to both primer pairs in the "three primer, two primer pair" methods is labeled with a detectable label in order to provide labeled amplification products. In the alternative or together with labeling the common primer, one or both of the non-common primer nucleic acids may also be labeled, or one or more labeled deoxynucleotide triphosphates may be incorporated into the amplification reaction. Numerous detectable labels for incorporation into nucleic acids are known to those of skill in the art. See, e.g., *Handbook of Fluorescent Probes and Research Products*, 9th ed., Molecular Probes, Inc., 2002, Chapter 8 ("Nucleic Acid Detection and Genomics Technology"). Illustrative fluorescent labels include xanthene dyes, naphthylamine dyes, coumarins, cyanine dyes and metal chelate dyes, such as fluorescein, rhodamine, rosamine, the BODIPY dyes (FL, TMR, and TR), dansyl, lanthanide cryptates, erbium, terbium and ruthenium chelates, e.g. squarates, and the like. Additionally, in certain embodiments, one or more fluorescent moieties can be energy transfer dyes such as those described in Waggoner et al., U.S. Pat. No. 6,008,373. In the exemplary embodiments described hereinafter, the reverse primer is labeled at the 5' end with 6-FAM (blue) fluorescent dye.

In the exemplary embodiments described herein, the ACE gene region contains a 287 bp insertion/deletion polymorphism, which is amplified by using a first forward primer (e.g., SEQ ID NO: 1) and a reverse primer (e.g., SEQ ID NO: 3), each of which flanks the 287 bp region. A fragment is also amplified from I/I and I/D genotypes with an insertion-specific second forward primer (e.g., SEQ ID NO: 2), which forms a second primer pair with the flanking reverse primer. The primers of the present invention can be manufactured using common methods of nucleic acid synthesis. For example, an automated nucleic acid synthesizer is preferred. In the most preferred embodiment, the first forward primer has the sequence 5'-CCA TCC TTT CTC CCA TTT CTC T-3' (SEQ ID NO: 1). The second forward primer has the sequence 5'-GGA TGG TCT CGA TCT CCT GA-3' (SEQ ID NO: 2). And the reverse primer is preferably labeled at the 5' end with a detectable label (e.g., 6-FAM (fluorescein)) and has the sequence 5'-(6-FAM)-CCT TAG CTC ACC TCT GCT TGT AA-3' (SEQ ID NO: 3).

Identification of At-Risk Individuals

The ACE genotype, and particularly the genotype regarding the I/D polymorphism, of an individual has been associated with various diseases, including myocardial infarction, coronary artery disease, ischemic and idiopathic dilated cardiomyopathy, sudden death in hypertrophic cardiomyopathy, and restenosis after percutaneous transluminal coronary angioplasty. Thus, the methods and compositions of the present invention can be used to identify such individuals in a clinical setting. In addition, identification of such individuals can also be used for ruling in or out certain individuals in various situations such as clinical trials and prospective or retrospective clinical studies, where the predisposition to a particular disease may be required for inclusion, or indicative of exclusion, from a selected group of individuals. The following is a list of exemplary diseases associated with the ACE I/D polymorphism:

| Disease | Genotype of Risk | Citation |
| --- | --- | --- |
| Cardiovascular disease | D/D | Circulation 1998, 97: 1780-1783 |
| Myocardial Ischemia and Myocardial infarction | D/D | J Am Coll Cardiol 1997, 29: 1468-73 |
| Aoronary Artery Disease | D/D | J Investing Med 1995, 43: 275-280 |
| Restenosis | D/D | Circulation 1997, 96: 56-60 |
| Coronary Artery Disease | D/D | Atherosclerosis, 1998, 139: 153-159 |
| Myocardial Infarction | D/D | Nature 1992, 359: 641-644 |
| Coronary Atherosclerosis | D/D | Br Heart J 1995; 584-591 |
| Stent Restenosis | D/D | Circulation 1998; 147-154 |
| Coronary Heart Disease | D/D | Proc Natl Acad Sci USA 1994; 3662-3665 |
| Essential Hypertension | D/D | Biochem Biophys Res Comm 1992; 9-15 |
| Myocardial Infarction | D/D | Clin Genetic 1992; 46: 94-101 |
| Atherosclerotic Plaque Calcification | D/D | JACC 1998; 31: 987-991 |
| Essential Hypertension | D/D | Circulation 2000; 101: 2060-2065 |
| Diabetic Nephropathy | D/D | J Diabetes Its Compl 2002; 16: 255-262 |

The ACE genotype of an individual has also been related to response to various clinical treatment regimens. Thus, the methods and compositions of the present invention can be used to identify an appropriate treatment regimen for an individual. In addition, identification of such individuals can also be used for ruling in or out certain individuals in various situations such as clinical trials and prospective or retrospective clinical studies, where response to a particular treatment regimen is required for inclusion, or indicative of exclusion, from a selected group of individuals. The following is a list of exemplary treatments associated with the ACE I/D polymorphism:

| Disease | Drug | Impact | ACE Genotype | Citation |
| --- | --- | --- | --- | --- |
| Coronary atherosclerosis | Fluvastatin | + | D/D | J Am Coll Cardiol 2000, 35: 89-95 |
| Restenosis | ACE Inhibitor (Imidapril) | + | I/I | Angiology 1999, 50: 811-822 |
| Congestive Heart Failure | Beta-Blocker | 0 | D/D | Circulation 2001; 103: 1644 |
| Chronic Cardiac Failure | ACE Inhibitor (Perindopril) | + | D/D | Ter Arkh 2002; 74: 54-58 |
| Restenosis | ACE Inhibitor (Quinapril) | + | D/D | Circ J 2002; 66: 311-316 |

EXAMPLE 1

This example describes one embodiment of reagents for performing the present methods. The person of ordinary skill in the art will realize that many variations of these reagents are possible without departing from the invention, and those variations are contemplated within the present invention.

PCR primers can be made according to standard and well-known techniques, such as by using an automated nucleic acid synthesizer. Primers can also be purchased commercially from various suppliers (e.g., Operon Technologies, Inc., Alameda, Calif.). Amplification primers for a particular gene are designed as follows. A first primer pair, comprising a first and second primer, is designed to flank a gene sequence, the presence of which indicates the presence of a gene variant, and the absence of which indicates the presence of a different gene variant. Each member of the first primer pair is also designed to initiate transcription towards the other member of the first primer pair. In this way, amplification will generate an amplicon having one length when the gene sequence is present, and a different length when the gene sequence is absent.

A third primer is designed to specifically bind only when the variant-specific gene sequence is present, and to function as a member of a second primer pair with the first or second primer. Each member of the second primer pair is also designed to initiate transcription towards the other member of the second primer pair. In this way, amplification will generate an amplicon only when the gene sequence is present.

The skilled artisan will acknowledge that such methods are generally applicable to any gene present as a plurality of alleles in a genome, in which the presence or absence of a specific sequence within the gene is to be distinguished. In an exemplary embodiment for identification of the ACE I/D polymorphism genotype, three primers (SEQ ID NOS: 1-3) were used. The reverse primer (SEQ ID NO: 3) was 5' labeled with 6-FAM (fluorescein).

An embodiment of a PCR "master mix" buffer was made according to the following formula: 50 units/ml of Taq polymerase, 400 µM each of dATP, dGTP, dCTP, and dTTP; and 3 mM MgCl$_2$.

An embodiment of loading mix was made by combining 23.9 µL of deionized formamide with 0.1 µL of Rox-500 for a total of 24 ul per sample to be tested. GeneScan ROX-500HD Size Standard can be obtained from commercial suppliers (Applied Biosystems). Other appropriate size standards (e.g., TAMRA-labeled standards) are also commercially available and known to those of ordinary skill in the art.

In a preferred embodiment the samples were prepared for the PCR reaction by combining 12.5 μL of PCR master mix, 0.25 μL of forward primer 1 (10 μM), 0.3 μL reverse primer (10 μM), 0.125 μL forward primer 2 (10 μM), 1.25 μL DMSO, and 9.575 μL of nuclease-free water. These amounts were per sample to be tested, for a total of 24 μL sample volume.

EXAMPLE 2

This example describes determination of a genotype from a DNA sample obtained from whole blood. Genomic DNA was extracted from whole blood by standard methods. 24 μL of PCR master mix was pipetted into a 0.2 ml PCR tubes and 1 μL of control samples (3 positive and 2 negative) and patient DNA was added to their respective tubes. The tubes were vortexed for about 5 seconds.

The samples were placed into a thermal cycler for PCR amplification when the cycler temperature reached 85° C. The PCR cycles were performed as follows:

| 1 | 94° C. | 2 min |
| 2 | 94° C. | 60 sec |
| 3 | 58° C. | 60 sec |
| 4 | 72° C. | 90 sec |
| 5 | go to step 2 | 29 cycles* |
| 6 | 72° C. | 15 min |
| 7 | 4° C. | hold |

*Typically 30 cycles is optimal, but 29-31 cycles maybe used if amplified products from 30 cycles are less than optimal.

After the PCR was complete, the samples were prepared for size fractionation by capillary electrophoresis on a commercially available Genetic Analyzer (ABI 310 Genetic Analyzer, Applied Biosystems, Inc., Foster City, Calif.). A 96 well plate tray with tubes was prepared. 24 μL of loading mix was placed into each sample tube with 1 μL of PCR products. The samples were vortexed briefly and placed in a 95° C. heat block for 3 minutes, and then immediately placed into a refrigerator for at least 3 minutes or until use. The samples were size fractionated according to manufacturer's instructions.

The person of ordinary skill in the art will realize that many methods of size fractionation are available (e.g., HPLC, manual gel electrophoresis, etc.) and that the samples can be size fractionated according to any of these methods without departing from the invention. Similarly, other methods besides size fractionation can be designed to determine the presence or absence of the indicating sequences and therefore yield the information provided by the methods, and those methods are also contemplated as being within the invention.

The various samples were then analyzed to correlate the PCR products with an ACE genotype. In those samples where a 157 bp fragment and a 410 bp fragment was present, and no 123 bp fragment was present, the genotype was assigned as insertion/insertion (I/I); in those samples where a 123 bp fragment, a 157 bp fragment, and a 410 bp fragment were present, the genotype was assigned as insertion/deletion (I/D); in those samples where only a 123 bp fragment is present, the genotype was assigned as deletion/deletion (D/D):

TABLE 1

| Genotype | Potential PCR Results: PCR Fragments Generated (base pairs) |
|---|---|
| I/I | 157, 410 |
| I/D | 123, 157, 410 |
| D/D | 123 |

The person of ordinary skill in the art will realize that primers with other sequences can be designed and used according to the invention and without departing from the invention. Thus, while the terms "123 bp fragment," "157 bp fragment," and "410 bp fragment" are used in this application, the person of ordinary skill in the art will realize that the number of base pairs in the fragment is not exact and can vary depending on the exact primer sequence used. Thus, for example, the "410 bp fragment" may contain a lesser or greater number of base pairs if amplified using a different primer. The other fragments may also vary in their size for the same reason. But what is important is that the fragments can be identified and correlated to one of the genotypes described above.

One or more of steps of the assays described herein, in any combination, are preferably performed in an automated fashion, typically using robotics, in order to provide for the processing of a large number of samples in a single batch run. Preferred forms of automation will provide for the preparation and separation of a plurality of labeled nucleic acids in small volumes. The term "small volumes" refers to volumes of liquids less than 2 ml, e.g., any volume from about 0.001 picoliters or about 0.001 μl, to any volume about 2 ml, 500 μl, 200 μl, 100 μl, 10 μl, 1 μl, 0.1 μl, 0.01 μl, or 0.001 μl. Additionally, capillary electrophoresis of the resulting amplification products is preferred over agarose gel electrophoresis for purposes of automated and/or high-throughput applications.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

The invention claimed is:

1. A method of determining an angiotensin converting enzyme (ACE) genotype in a sample, comprising:
   amplifying DNA in a single amplification reaction from the sample with a first pair of flanking primers that hybridize to nucleic acid sequences flanking an ACE gene sequence, and a third primer that specifically binds to said ACE gene sequence and together with one of the flanking primers forms a second pair of primers; and
   detecting a homozygous ACE genotype by the production of one or two amplification products and a heterozygous ACE genotype by the production of three amplification products.

2. The method of claim 1 wherein said amplification reaction is by polymerase chain reaction.

3. The method of claim 1 wherein the sample is a human sample.

4. The method of claim 3 wherein the method distinguishes between genotypes selected from the group consisting of: insertion/insertion, insertion/deletion, deletion/deletion.

5. The method of claim 3 wherein the DNA is un-degraded DNA.

6. The method of claim 5 wherein the sample is a tissue sample.

7. The method of claim 6 wherein the sample is selected from the group consisting of: blood, cultured cells, cells derived from amniotic fluid, and cells derived from chorionic villi.

8. The method of claim 1 wherein the sample is blood.

9. The method of claim 3 wherein the ACE sequence resides on Intron 16 of chromosome 17q23.

10. The method of claim 3 wherein the ACE sequence is a 287 base pair nonsense DNA domain.

11. The method of claim 3 wherein the first pair of flanking primers have the nucleic acid sequences 5'-CCA TCC TTT CTC CCA TTT CTC T-3' (SEQ ID NO: 1) and 5'-GGA TGG TCT CGA TCT CCT GA-3' (SEQ ID NO: 2); and the third primer has the nucleic acid sequence 5'-CCT TAG CTC ACC TCT GCT TGT AA-3'(SEQ ID NO: 3).

12. The method of claim 3 wherein the DNA sample is from a source selected from the group consisting of: the endothelium of blood vessels, epithelial cells, blood mononuclear cells, macrophages, male germinal cells, and a biological fluid.

13. The method of claim 3 wherein the nucleic acid products consist of a first nucleic acid fragment of approximately 123 base pairs, a second nucleic acid fragment of approximately 157 base pairs, and a third nucleic acid fragment of approximately 410 base pairs.

14. The method of claim 11 wherein the nucleic acid products consist of a first nucleic acid fragment of 123 base pairs, a second nucleic acid fragment of 157 base pairs, and a third nucleic acid fragment of 410 base pairs.

15. The method of claim 14 wherein:
when the first nucleic acid fragment is not present and the second and third nucleic acid fragments are present, the genotype is I/I;
when the first, second, and third nucleic acid fragments are present, the genotype is I/D; and
when the first nucleic acid fragment is present and the second and third nucleic acid fragments are not present, the genotype is D/D.

16. The method of claim 1 wherein the first pair of flanking primers have the nucleic acid sequences 5'-CCA TCC TTT CTC CCA TTT CTC T-3' (SEQ ID NO: 1) and 5'-GGA TGG TCT CGA TCT CCT GA-3' (SEQ ID NO: 2); and the third primer has the nucleic acid sequence 5'-CCT TAG CTC ACC TCT GCT TGT AA-3' (SEQ ID NO: 3).

17. The method of claim 16 wherein the amplification is by polymerase chain reaction.

18. The method of claim 17 wherein the method distinguishes between genotypes selected from the group consisting of: insertion/insertion, insertion/deletion, deletion/deletion.

19. The method of claim 17 wherein the ACE sequence resides on Intron 16 of chromosome 17q23.

20. The method of claim 17 wherein the ACE sequence is a 287 base pair nonsense DNA domain.

21. The method of claim 17 wherein the DNA sample is from a source selected from the group consisting of: the endothelium of blood vessels, epithelial cells, blood mononuclear cells, macrophages, male germinal cells, and a biological fluid.

22. The method of claim 17 wherein the nucleic acid products consist of a first nucleic acid fragment of 123 base pairs, a second nucleic acid fragment of 157 base pairs, and a third nucleic acid fragment of 410 base pairs.

23. The method of claim 22 wherein:
when the first nucleic acid fragment is not present and the second and third nucleic acid fragments are present, the genotype is I/I;
when the first, second, and third nucleic acid fragments are present, the genotype is I/D; and
when the first nucleic acid fragment is present and the second and third nucleic acid fragments are not present, the genotype is D/D.

24. A method for identifying a patient with a heightened risk of suffering from a disease comprising:
determining the angiotensin converting enzyme (ACE) genotype in a sample from the patient by amplifying DNA in a single amplification reaction from the sample with a first pair of flanking primers that hybridize to nucleic acid sequences flanking an ACE gene sequence, the presence of which indicates the presence of a first ACE gene variant, and the absence of which indicates the presence of a second ACE gene variant, and a third primer that specifically binds to said ACE gene sequence and together with one of the flanking primers forms a second pair of primers;
detecting a homozygous ACE genotype by the production of one or two amplification products and a heterozygous ACE genotype by the production of three amplification products; and
correlating the ACE genotype of the patient with a treatment regimen designed to treat or prevent one or more diseases selected from the group consisting of: myocardial infarction, ischemic and idiopathic dilated cardiomyopathy, sudden death in hypertrophic cardiomyopathy, coronary atherosclerosis, and restenosis after percutaneous transluminal coronary angioplasty.

25. The method of claim 24 wherein the treatment regimen is designed to treat myocardial infarction or coronary atherosclerosis.

26. The method of claim 24 wherein the method distinguishes between genotypes selected from the group consisting of insertion/insertion, insertion/deletion, deletion/deletion.

27. The method of claim 24 wherein the genotype is determined by detecting the presence or absence of each of three nucleic acid products of the amplification reaction.

28. The method of claim 25 wherein the pair of flanking primers have the nucleic acid sequences 5'-CCA TCC TTT CTC CCA TTT CTC T-3' (SEQ ID NO: 1) and 5'-GGA TGG TCT CGA TCT CCT GA-3' (SEQ ID NO: 2); and the third primer has the nucleic acid sequence 5'-CCT TAG CTC ACC TCT GCT TGT AA-3' (SEQ ID NO: 3).

29. A method of determining a genotype for a gene of interest in a sample, comprising:
amplifying DNA in a single amplification reaction from the sample with a first pair of flanking primers that hybridize to nucleic acid sequences flanking a sequence in said gene of interest, the presence of which indicates the presence of a first gene variant, and the absence of which indicates the presence of a second gene variant, and a third primer that specifically binds to said gene sequence and together with one of the flanking primers forms a second pair of primers; and
detecting a homozygous genotype by the production of one or two amplification products and a heterozygous genotype by the production of three amplification products.

30. The method of claim 29 wherein said amplification is by polymerase chain reaction.

31. The method of claim 29 wherein the sample is a human sample.

32. The method of claim 29 wherein the DNA sample is from a source selected from the group consisting of: the endothelium of blood vessels, epithelial cells, blood mononuclear cells, macrophages, male germinal cells, and a biological fluid.

33. The method of claim 29 wherein the nucleic acid products consist of a first nucleic acid fragment of approximately 123 base pairs, a second nucleic acid fragment of approximately 157 base pairs, and a third nucleic acid fragment of approximately 410 base pairs.

34. The method of claim 29 wherein the nucleic acid products consist of a first nucleic acid fragment of 123 base pairs, a second nucleic acid fragment of 157 base pairs, and a third nucleic acid fragment of 410 base pairs.

\* \* \* \* \*

UNITED STATES PATENT AND TRADEMARK OFFICE
CERTIFICATE OF CORRECTION

PATENT NO. : 7,514,213 B2  Page 1 of 1
APPLICATION NO. : 10/714508
DATED : April 7, 2009
INVENTOR(S) : Kevin Z. Qu et al.

It is certified that error appears in the above-identified patent and that said Letters Patent is hereby corrected as shown below:

On the Title Page

Item [*] Notice: Subject to any disclaimer, the term of this patent is extended or adjusted under 35 U.S.C. 154(b) by (938) days Delete the phrase "by 938 days" and insert -- by 1169 days --

Signed and Sealed this

First Day of June, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccatcctttc tcccatttct ct                                            22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggatggtctc gatctcctga                                               20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccttagctca cctctgcttg taa                                           23

<210> SEQ ID NO 4
<211> LENGTH: 1856
<212> TYPE: DNA
<213> ORGANISM: Homo sapiens

<400> SEQUENCE: 4
gtgagagctc atgtgcaggc tgagtgagag gcgagggctg ggactggcat ggggcccggg     60
ggtgctgggt gagagcacag agttgggctc cctcgctct tggggtcagc gtgcccagga    120
aatgcccttt cttgttttcc acgagggggg cttctctgcc cactgagagc cggcacctac    180
ttcataccat gccccgatca gctgcccctc cctcagaacc gccctctgct taagggtgtc    240
cactctctcc tgtcctctct gcatgccgcc cctcagagca gcgggatctc aaagttatat    300
ttcatgggct tggactccaa atgggggaa ctcggggaca ctagctcccc ccggcctcct    360
ttcgtgaccc tgcccttgac ttcctcacct tctctgtctt tcctgagccc ctctcccagc    420
atgtgactga taaggaaatt gagtcacaca gcccctgaaa gcgccagact agaacctgag    480
cctctgattc ctctcacttc cctccccac cctgccactt cctactggat agaagtagac    540
agctcttgac tgtcctcttt tctccccact ggctggtcct tcttagcccc agcccgtttg    600
aaagagctca ccccgacac aaggacccgc acacagatac ctcccagctc cctctcaacc    660 cacccttcc agggttggag aacttgaggc ataaacattc ttcatgagg aatctccacc    720 cagaaatggg tctttctggc ccccagccca gctcccacat tagaacaatg acaaatagaa    780
ggggaaatgg aaaataaaca ggagaaacgg ttttcccagg acagggtttg gcctacaagt    840

-continued

```
tgtggatgtg ggtacccatg ccaagtgtga ggggaggctg gccgggtgtg gtggctcatg    900
ctctaatccc agcactttgg gaggccaagg tgagtagatc acttgaggcc gggagtttga    960
gaccagcctg gccaacatgg tgaaacccca tctgtactaa aaatacaaaa gttagctggg   1020
cgtggtggta gatgcctgta gtcccagcta cttgggaggc tgaggcatga gaatcgcttg   1080
agcccagcca gggcaataca gcaagacccc gtctctacaa ataaaataca aaaaattagt   1140
tggatgtggt ggtgcatgcc tgtagtccta gctgctaggg aggctgagat ggaaggattg   1200
cttgagcctg ggaggtcaag gctgcagtga gccgagatgg cgccactgca ctccagcctg   1260
ggcaacagag tgagaccctg tctcagaaag aaaaaaaaaa aaaaaggaga ggagagagac   1320
tcaagcacgc ccctcacagg actgctgagg ccctgcaggt gtctgcagca tgtgcccagg   1380
ccggggactc tgtaagccac tgctggagac cactcccatc ctttctccca tttctctaga   1440
cctgctgcct atacagtcac ttttttttttt tttttgagac ggagtctcgc tctgtcgccc   1500
aggctggagt gcagtggcgg gatctcggct cactgcaacg tccgcctccc gggttcacgc   1560
cattctcctg cctcagcctc ccaagtagct gggaccacag cgcccgccac tacgcccggc   1620 taatttttg tatttttagt agagacgggg tttcaccgtt ttagccggga tggtctcgat   1680
ctcctgacct cgtgatccgc ccgcctcggc ctcccaaagt gctgggatta caggcgtgat   1740
acagtcactt ttatgtggtt tcgccaattt tattccagct ctgaaattct ctgagctccc   1800
cttacaagca gaggtgagct aagggctgga gctcaagcca ttcaaccccc taccag       1856
```

<210> SEQ ID NO 5
<211> LENGTH: 278
<212> TYPE: DNA
<213> ORGANISM: Homo sapiens

<400> SEQUENCE: 5

```
atacagtcac tttttttttt tttttgagac ggagtctcgc tctgtcgccc aggctggagt     60
gatctcggct cactgcaacg tccgcctccc gggttcacgc cattctcctg cctcagcctc    120
ccaagtagct gggaccacag cgcccgccac tacgcccggc taatttttg tatttttagt    180 agagacgggg tttcaccgtt ttagccggga tggtctcgat ctcctgacct cgtgatccgc    240
ccgcctcggc ctcccaaagt gctgggatta caggcgtg                            278
```